(12) United States Patent
Sammarco

(10) Patent No.: US 10,226,286 B2
(45) Date of Patent: Mar. 12, 2019

(54) DEVICES AND METHODS FOR BONE FIXATION USING AXIAL IMPLANTS

(71) Applicant: Extremity Medical, LLC, Parsippany, NJ (US)

(72) Inventor: Vincent James Sammarco, Cincinnati, OH (US)

(73) Assignee: Extremity Medical, LLC, Parsippany, NJ (US)

( * ) Notice: Subject to any disclaimer, the term of this patent is extended or adjusted under 35 U.S.C. 154(b) by 0 days.

(21) Appl. No.: 15/359,178

(22) Filed: Nov. 22, 2016

(65) Prior Publication Data

US 2017/0071642 A1    Mar. 16, 2017

Related U.S. Application Data

(60) Continuation of application No. 14/599,713, filed on Jan. 19, 2015, now Pat. No. 9,498,265, which is a
(Continued)

(51) Int. Cl.
| | | |
|---|---|---|
| *A61B 17/72* | (2006.01) | |
| *A61B 17/86* | (2006.01) | |
| *A61B 17/17* | (2006.01) | |
| *A61B 17/15* | (2006.01) | |
| *A61B 17/16* | (2006.01) | |

(Continued)

(52) U.S. Cl.
CPC ...... *A61B 17/7241* (2013.01); *A61B 17/1725* (2013.01); *A61B 17/7225* (2013.01); *A61B 17/7233* (2013.01); *A61B 17/7291* (2013.01); *A61B 17/86* (2013.01); *A61B 17/8605* (2013.01); *A61B 17/8625* (2013.01); *A61B 17/8635* (2013.01); *A61B 17/151* (2013.01); *A61B 17/1657* (2013.01); *A61B 17/1697* (2013.01); *A61B 17/1775* (2016.11); *A61B 17/864* (2013.01); *A61B 17/8875* (2013.01);
(Continued)

(58) Field of Classification Search
CPC ............ A61B 17/7291; A61B 17/8605; A61B 17/8625; A61B 17/8635
See application file for complete search history.

(56) References Cited

U.S. PATENT DOCUMENTS 3,763,855 A * 10/1973 McAtee ................. A61B 17/72
                                                           606/64
4,281,649 A *  8/1981 Derweduwen ..... A61B 17/1725
                                                           606/64
(Continued)

*Primary Examiner* — Christopher Beccia
(74) *Attorney, Agent, or Firm* — Kelley Drye & Warren LLP

(57) ABSTRACT

The invention comprises a method for fixating bones in the foot by aligning the bones in their desired position, inserting a screw in the aligned bones, inserting at least one transverse element near the head or tip of the screw, and tightening the screw to compress the bones. The screw comprises a shaft having first and second ends with spirally wound screw threads beginning near the first end and extending along the shaft. Advantageously, the screw is cannulated and screw threads are formed on an interior surface of the cannulation. Illustratively, the transverse elements may be staples, open-ended washers, or open-ended nuts. Reduction instruments and drill guides used in the invention are also disclosed.

17 Claims, 13 Drawing Sheets

Related U.S. Application Data division of application No. 13/712,282, filed on Dec. 12, 2012, now abandoned.

(60) Provisional application No. 61/569,464, filed on Dec. 12, 2011.

(51) Int. Cl.
 *A61B 17/88* (2006.01)
 *A61B 17/56* (2006.01)
 *A61B 17/68* (2006.01)

(52) U.S. Cl.
 CPC ..... *A61B 17/8897* (2013.01); *A61B 2017/564* (2013.01); *A61B 2017/681* (2013.01)

(56) References Cited

U.S. PATENT DOCUMENTS

| | | | | |
|---|---|---|---|---|
| 6,517,541 | B1* | 2/2003 | Sesic | A61B 17/72 606/62 |
| 8,585,744 | B2* | 11/2013 | Duggal | A61B 17/683 606/301 |
| 2004/0204713 | A1* | 10/2004 | Abdou | A61B 17/8004 606/71 |
| 2005/0143735 | A1* | 6/2005 | Kyle | A61B 17/742 606/60 |
| 2009/0062797 | A1* | 3/2009 | Huebner | A61B 17/7225 606/62 |
| 2009/0099571 | A1* | 4/2009 | Cresina | A61B 17/17 606/96 |

* cited by examiner

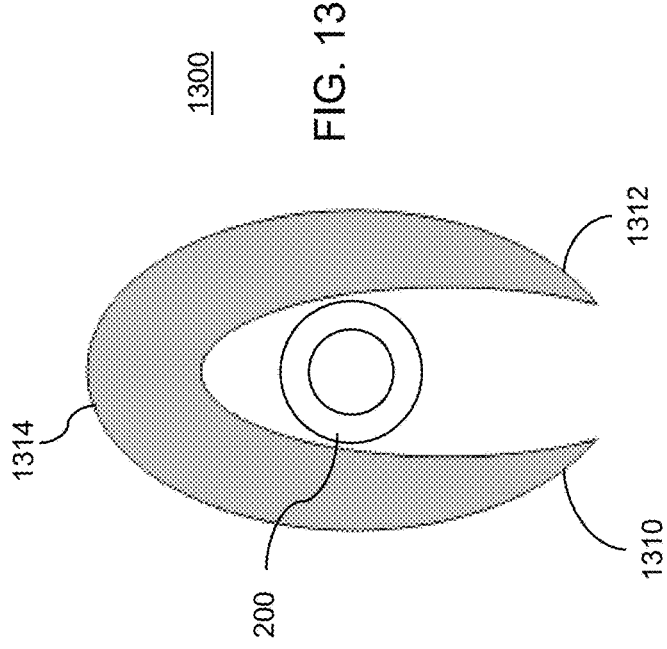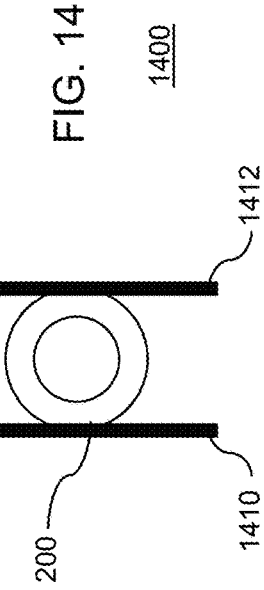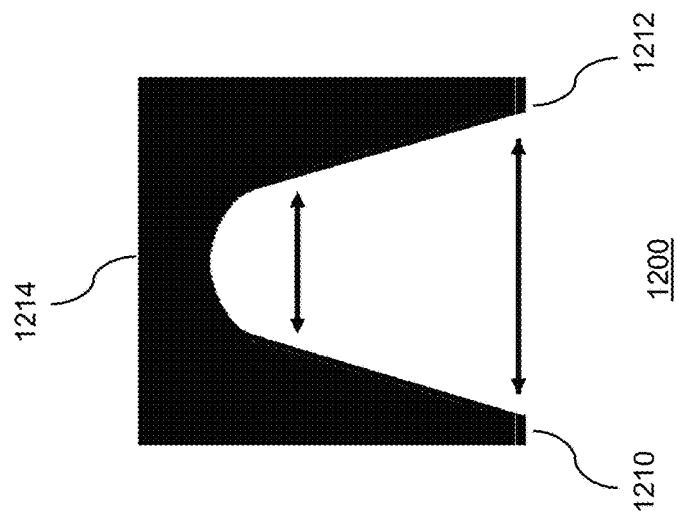

DEVICES AND METHODS FOR BONE FIXATION USING AXIAL IMPLANTS

CROSS REFERENCE TO RELATED APPLICATION

This application is a continuation of U.S. application Ser. No. 14/599,713, filed Jan. 19, 2015, which claims the benefit of divisional of U.S. application Ser. No. 13/712,282, filed on Dec. 12, 2012, which claims the benefit of U.S. Provisional Application No. 61/569,464, filed Dec. 12, 2011. The entire contents of these applications are incorporated herein by reference.

BACKGROUND

This invention relates to the field of orthopedic implant devices. A typical application is as an intramedullary fixation assembly used for the fixation of bones and the correction of deformities in the foot.

Orthopedic implant devices such as intramedullary nails, plates, rods and screws are often used to repair or reconstruct bones and joints affected by deformity and disease such as Charcot arthopathy caused by diabetes in some patients. Charcot arthopathy (or Charcot foot) is a destructive process affecting many regions including joints of the foot and ankle in diabetics. Charcot arthopathy can affect any joint in the body but is often seen in the foot. In the foot, the Charcot process typically affects the tarsal and metatarsal bones and the tarsometatarsal and intertarsal joints which causes the foot to lose its arch. This causes fragmentation, dislocation and fractures that eventually progress to deformity, instability and bony prominences. Foot ulcers may develop which often lead to deep infection and sometimes amputation.

FIG. 1 depicts a human foot 100 afflicted with Charcot arthopathy. Phalanges 110, the first metatarsal 120, medial cuneiform 130, navicular 140, and talus 150 bones are depicted in foot 100. The deformity in the foot will be apparent.

Early treatment for Charcot foot includes the use of therapeutic footwear, immobilization of the foot, and/or non-weightbearing treatment. Surgical treatments include orthopedic fixation devices that fixate the bones in order to fuse them into a stable mass. These orthopedic implant devices realign bone segments and hold them together in compression until healing occurs, resulting in a stable mass.

Infection and complications are a major concern in these procedures. Wound closure is technically demanding for the surgeon, and devices that add surface prominence such as plates or exposed screws, add to the difficulty by requiring greater tissue tension during incision reapproximation. This increases the risk of post-operative wound infections and dehiscence that may ultimately result in limb amputation.

There is therefore a need for improvements in intramedullary fixation assembly and methods of use that overcome some or all of the previously described drawbacks of prior art fixation assemblies and processes.

SUMMARY

The present invention is improved devices and methods for bone fixation.

The improved devices include a screw for use in fixating the bones and the combination of the screw with at least one transverse element for use in compressing the bones. In a preferred embodiment, the screw comprises a shaft having first and second ends with spirally wound screw threads beginning near the first end and extending along the shaft. Advantageously the screw is cannulated and screw threads are formed on an interior surface of the cannulation.

When the screw is implanted in a patient's foot, at least one transverse element is secured to the screw near its first or second end. By way of example but not limitation, the transverse elements may be staples, open-ended washers, or open-ended nuts. The screw is then tightened causing the bones along the screw to be compressed.

Broadly, the methods of the invention comprise aligning the bones in their desired position, inserting a screw in the aligned bones, inserting at least one transverse element near the head or tip of the screw, and tightening the screw. Further details of the process are set forth below.

Instruments are also disclosed for use in practicing the invention. These include reduction instruments for use in aligning the bones and a drill guide for drilling holes adjacent the screw where one or more transverse elements may be inserted.

Numerous variations may be practiced in the preferred embodiment.

BRIEF DESCRIPTION OF THE DRAWINGS

These and other objects and advantages of the present invention will be apparent to those of ordinary skill in the art in view of the following detailed description in which:

FIGS. 12-14 depict several transverse elements that may be used in the practice of the invention.

DETAILED DESCRIPTION

Figure 1:
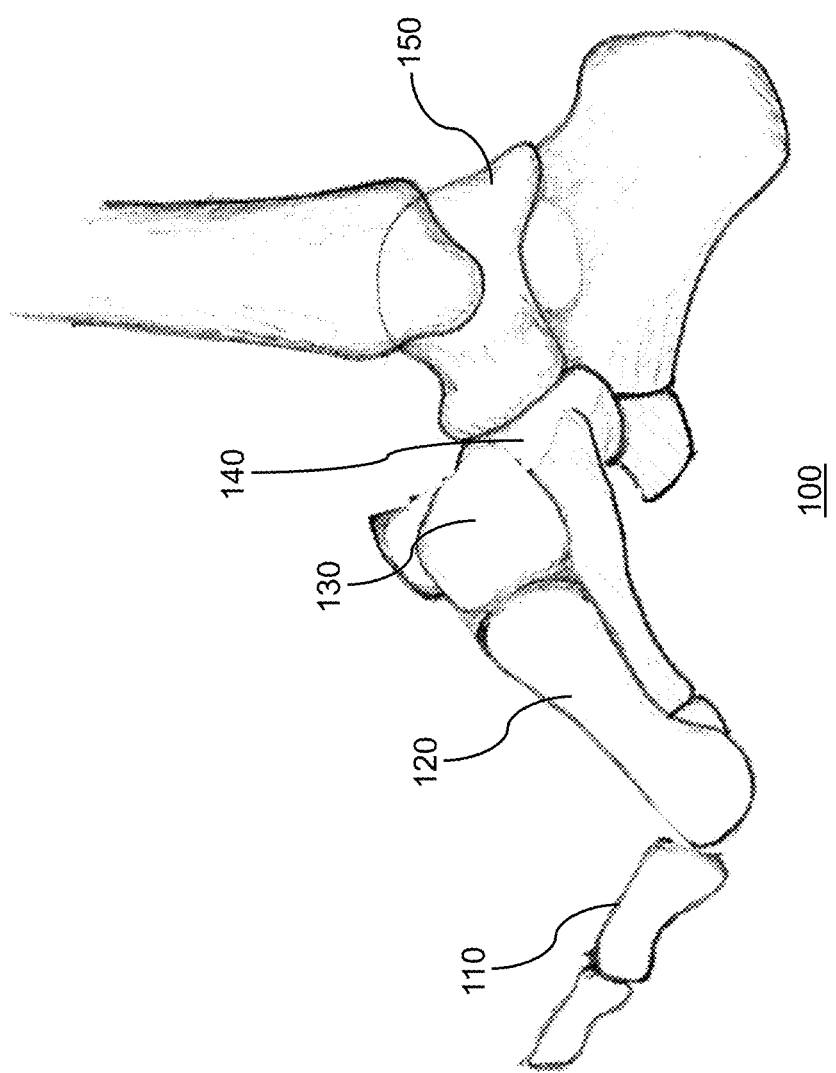
FIG. 1 depicts a human foot afflicted with Charcot arthopathy.
Figure 2:
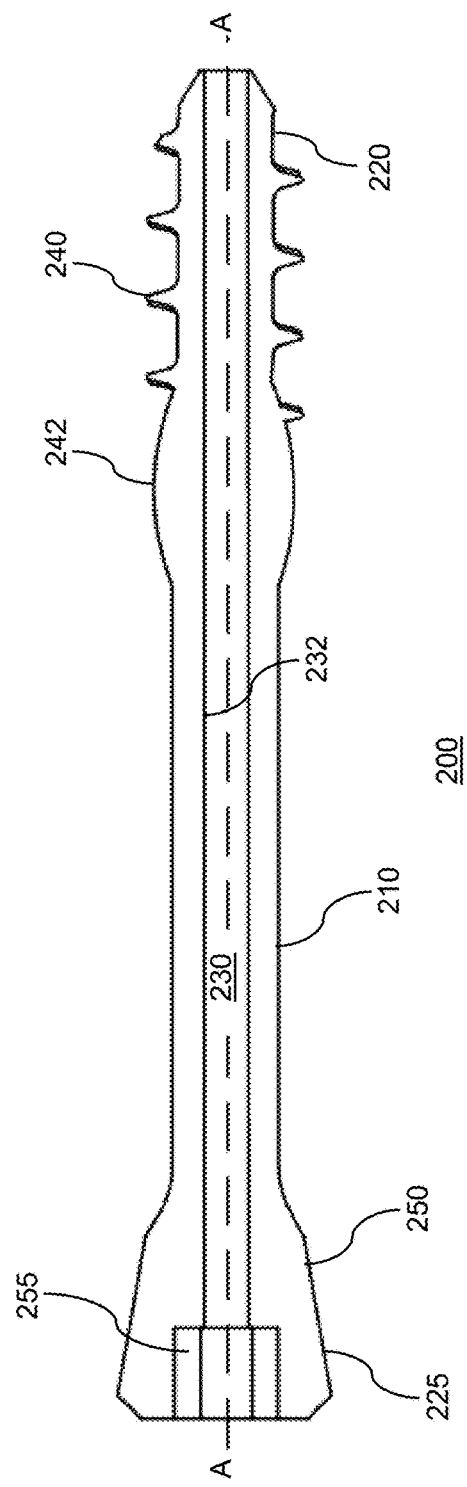
FIG. 2 is a cross-section of an illustrative embodiment of a screw of the present invention.

FIG. 2 is a cross-section of an illustrative embodiment of a screw 200 that may be used in the practice of the invention. Screw 200 has an elongated shaft 210 having first and second ends 220, 225 and a longitudinal axis A-A extending along the shaft. Preferably, the shaft is cannulated having a bore 230 that extends from first end 220 to second end 225. On an exterior portion of the shaft near the first end 220 are spirally wound threads 240 that begin at approximately the first end 220 of the shaft. There may be a head 250 on the shaft at its second end 225. The diameter of the head may be wider than the diameter of the shaft. Alternatively, the head may be set off from the remainder of the shaft by a recess that circumscribes the shaft such as shown at 252 in FIG. 6. The invention may also be practiced using a screw in which there are threads at the second end of the screw in place of a head.

The head of the shaft includes a recess 255 open to the end of the shaft that is shaped to receive an instrument such as a screw driver or wrench in driving engagement. For example, by way of illustration but not limitation, the recess may be hexagonal in shape so as to receive a hexagonally shaped wrench similar to an Allen wrench or the like; or the recess may be slotted so as to receive the slotted blade of a screw driver. Alternatively, there may be no recess in the head; and the head may be shaped, for example, in a hexagon, to receive an instrument such as a socket wrench or the like.

Optionally, numerous other refinements may be made in the construction of the screw. For example, the screw may be reinforced at points where forces are concentrated during use of the screw such as the point 242 where exterior screw threads 240 end. The threads may also be tapered at point 242. Spirally wound threads may also be formed on an interior surface 232 of the bore 230. Such threads can facilitate extraction of the screw if that becomes desirable. The screw may also be treated by various processes to increase its strength.

Figure 3:
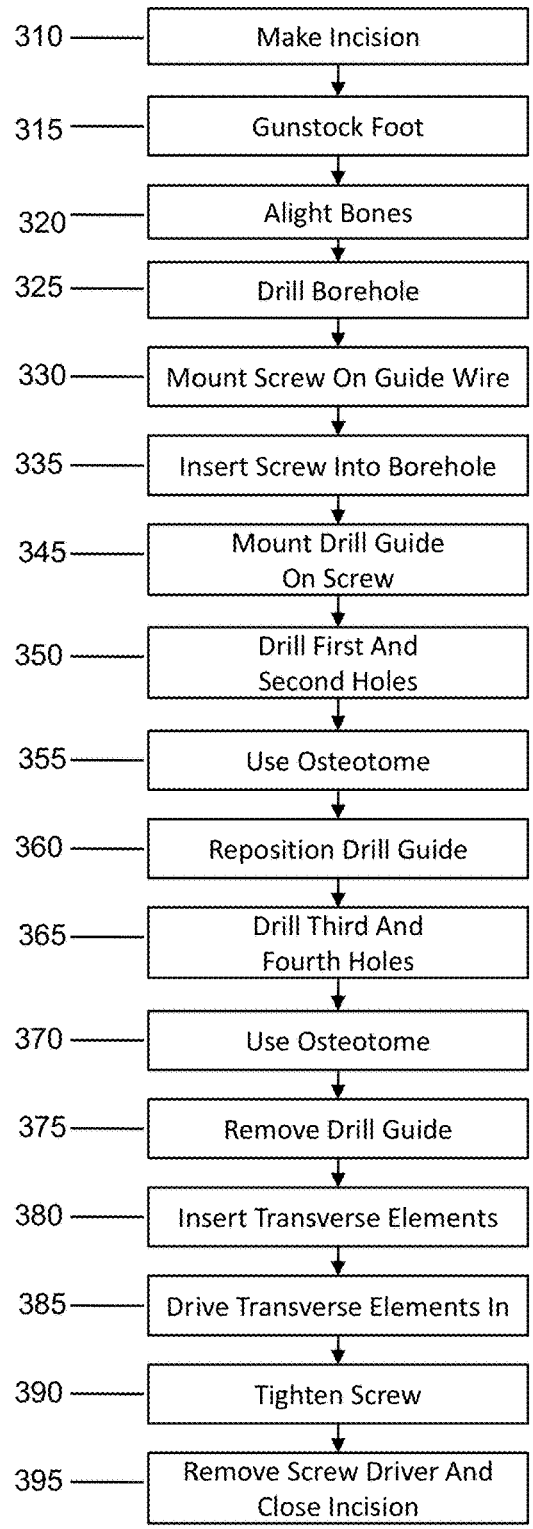
FIG. 3 is a flow chart depicting illustrative steps of an embodiment of the invention.

FIG. 3 is a flow chart depicting illustrative steps of an embodiment of the invention used to treat Charcot arthopathy. It will be understood that the flow chart is only illustrative, that the order of execution of some steps may vary, and that some steps may not need to be used in the treatment of a particular patient in accordance with the invention. Initially, an incision is made in the foot at step 310 to expose the metatarsal. Illustratively, the incision is a doral Lis Franc incision. Next, the foot is "gunstocked" at step 315. The bones of the foot, typically the metatarsal, cuneiform, navicular and talus are then aligned at step 315 in the desired final position using a guide wire (e.g., a K-wire) to secure the bones in the desired alignment.

Figure 4:
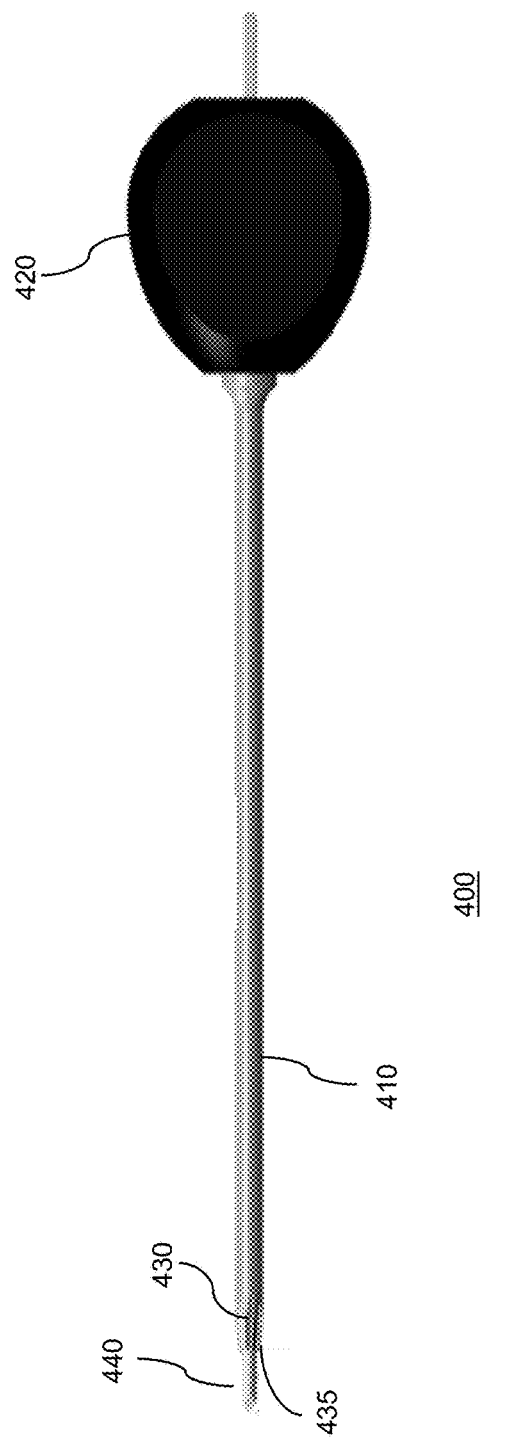
FIG. 4 depicts a reduction instrument used in the practice of the invention.

Illustratively, the guide wire is inserted into the bones using a reduction instrument such as instrument 400 of FIG. 4. Instrument 400 comprises a hollow sleeve 410 mounted on a handle 420. Sleeve 410 has a cutting tip 430 on the end of the sleeve remote from the handle. A bore 435 extends through sleeve 410 and handle 420 having an inside diameter that is large enough to allow passage of a guide wire 440.

The diameter of guide wire 440 that may be used in the practice of the invention can vary considerably depending on the patient and the surgeon's preferences. Illustratively, the diameter is in the range of approximately 1.0 to 4.0 millimeters (mm). Different sleeve lengths may be used in the practice of the invention depending on the size of the bones that are to be aligned. Advantageously, instrument 400 is used with guide wire 440 sticking through tip 430, which allows guide wire 440 to be seated and unseated in the bone. Advantageously, the other end of guide wire 440 is keyed in handle 420 so that it can be easily maneuvered by the handle.

Figure 5:
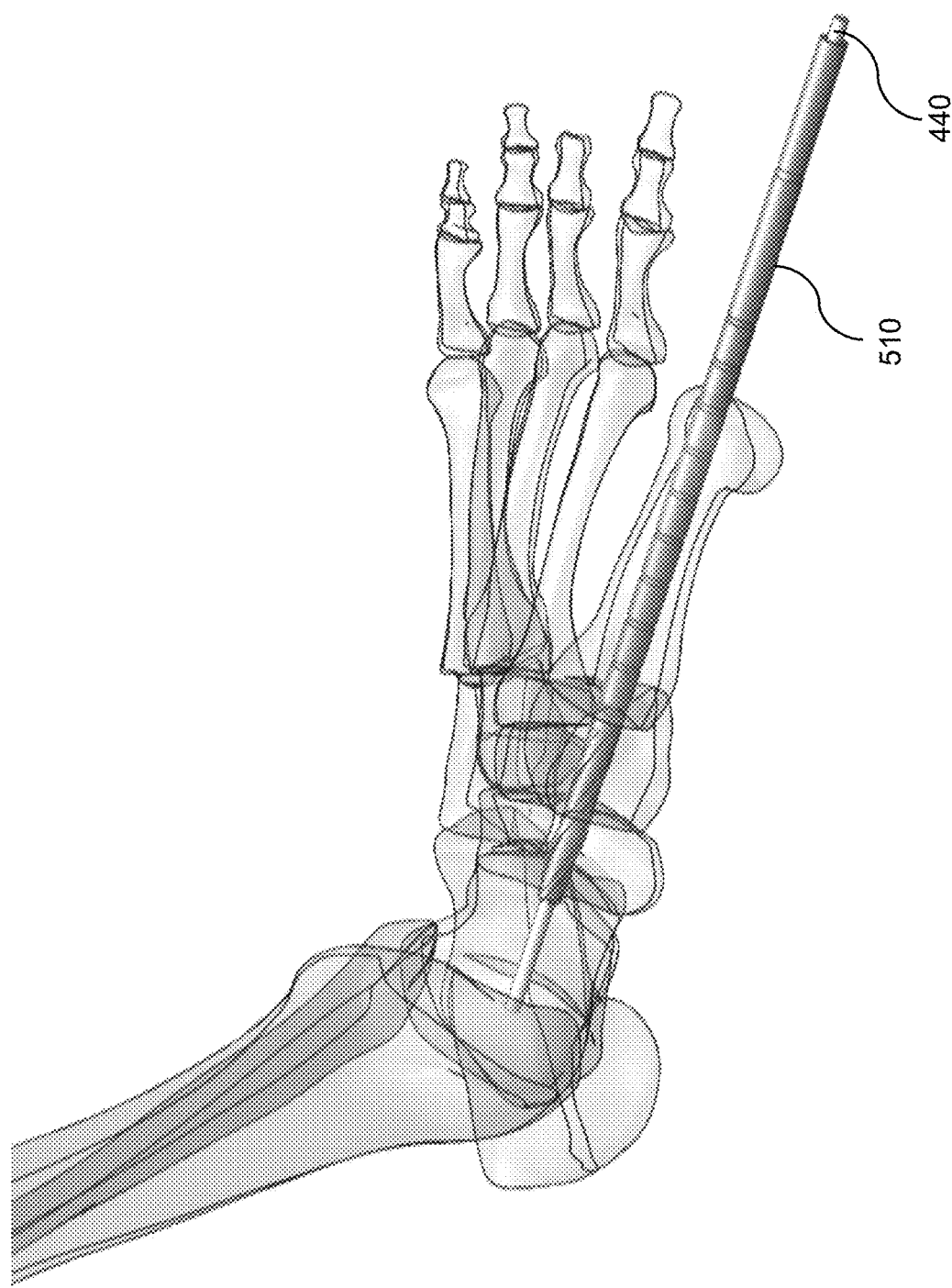
FIGS. 5, 6, 8-11, and 15 depict details of certain of the steps of FIG. 3.
Figure 6:
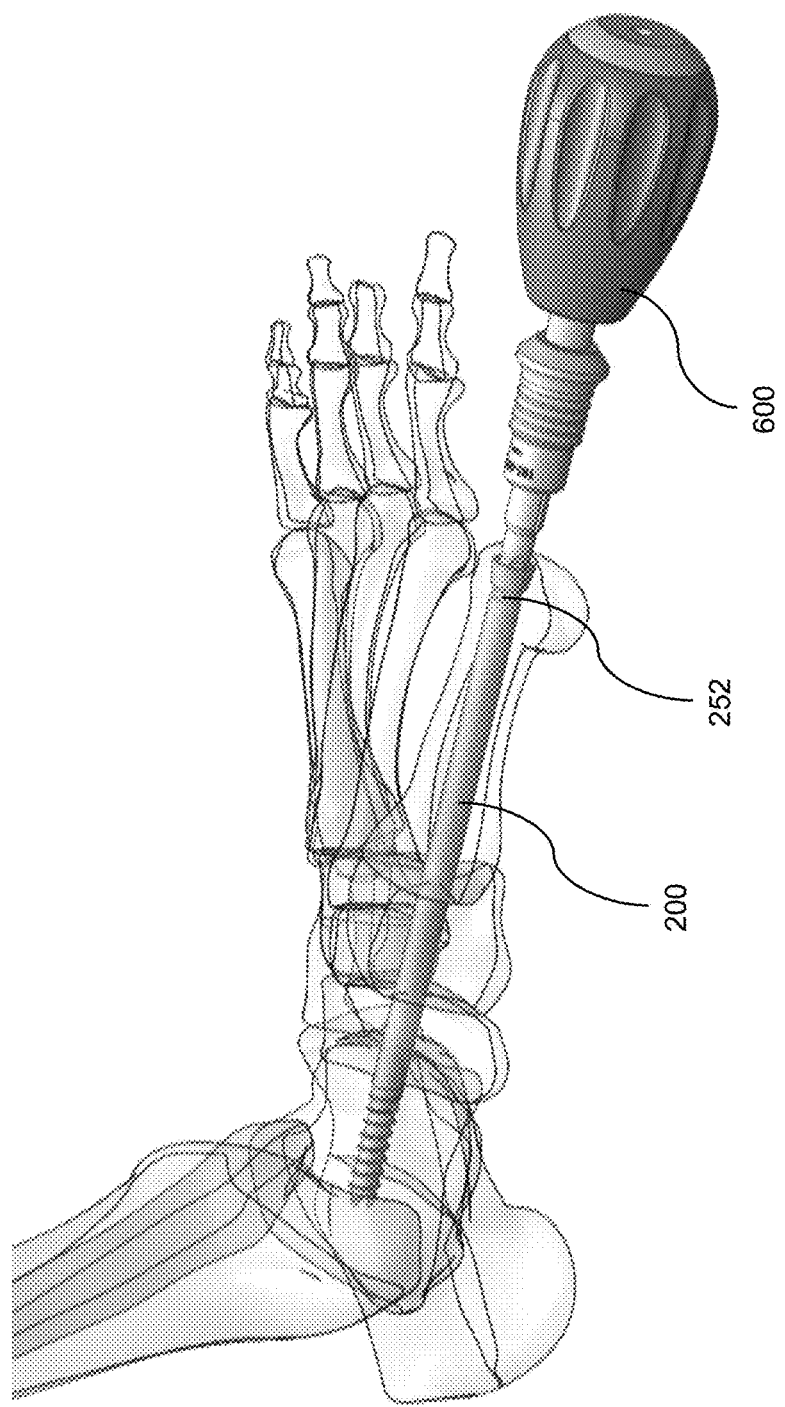

After the bones are aligned on the guide wire as described above, instrument 400 is removed from the guide wire. Returning to the flow chart of FIG. 3, a drill bit is then mounted on the guide wire; and a borehole is drilled at step 325 through one or more of the aligned bones. This step is illustrated in FIG. 5 which depicts drill bit 510 on guide wire 440 boring a hole in the aligned bones, in this example, the first metatarsal, the medial cuneiform, the navicular, and the talus bones of a left foot. The drill is then removed; and a cannulated screw such as screw 200 of FIG. 2 is mounted on the guide wire at step 330. Screw 200 is then screwed into the borehole at step 335 using a screw driver 600 as shown in FIG. 6.

A drill guide is then mounted on the screw at step 345. The drill guide is used at step 350 to guide a drill bit in forming first and second holes on opposite sides of the screw at a first position that typically is just below the head of the screw. In forming these holes, the drill bit breaks the cortex of the bone on either side of the screw at the first position. The drill guide is also used at step 355 to guide an osteotome that cuts the cortex of the bone between the first and second holes at the first position. Next, an element of the drill guide is positioned at a second position above the threaded portion of the screw at step 360. This element is then used at step 365 to form at least one pair of third and fourth holes on opposite sides of the screw at the second position. Again, the drill bit breaks the cortex of the bone on either side of the screw in the second position. This element is also used at step 370 to guide an osteotome that cuts the cortex of the bone between the third and fourth holes at the second position. The drill guide is then withdrawn at step 375.

Figure 7:
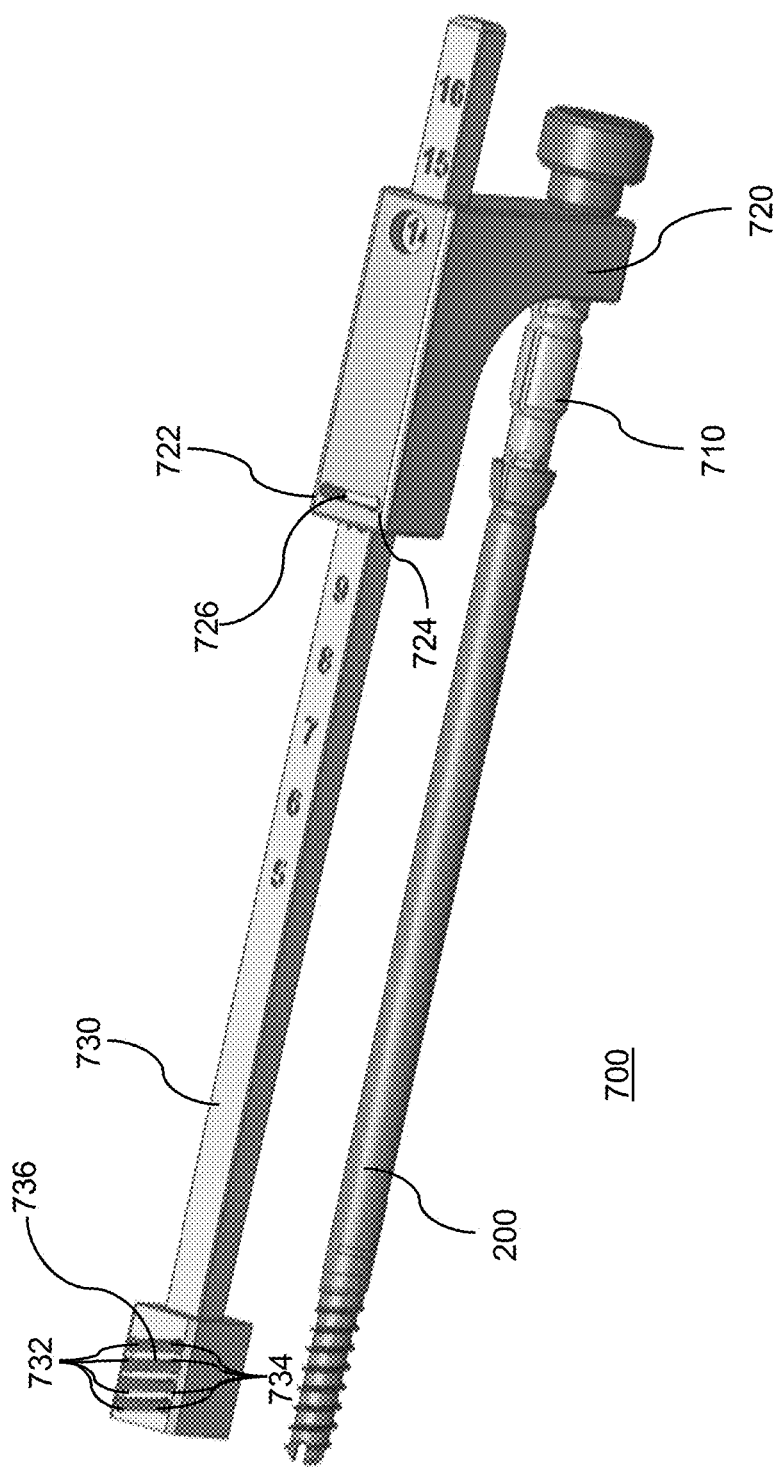
FIG. 7 depicts a drill guide used in the practice of the invention.

The drill guide is shown as guide 700 in FIG. 7 and its use is depicted in FIGS. 8-11. Guide 700 comprises a screw mount 710 that is screwed or clamped onto screw 200 so that it is aligned with the longitudinal axis A-A of screw 200. The guide further comprises a bracket 720 that is mounted on the screw mount 710 and an extension arm 730 that is mounted on bracket 720 so that the arm extends parallel to the longitudinal axis of screw 200. Bracket 720 encloses first and second holes 722, 724 and a slot 726 that extends between the first and second holes. Extension arm 730 encloses several sets of third and fourth holes 732, 734 and a slot 736 that extends between the third and fourth holes. The first and second holes are located in bracket 720 at a position such that when bracket 720 is securely mounted on screw 200, the holes are on opposite sides of the screw at the first position on the screw. Extension arm 730 can be positioned so that the third and fourth holes are on opposite sides of the screw at the second position on the screw. The several sets of holes 732, 734 and slot 736 make it possible to locate several transverse elements at the second position. A ruler on the extension arm allows the surgeon to locate the second position with precision.

Figure 8:
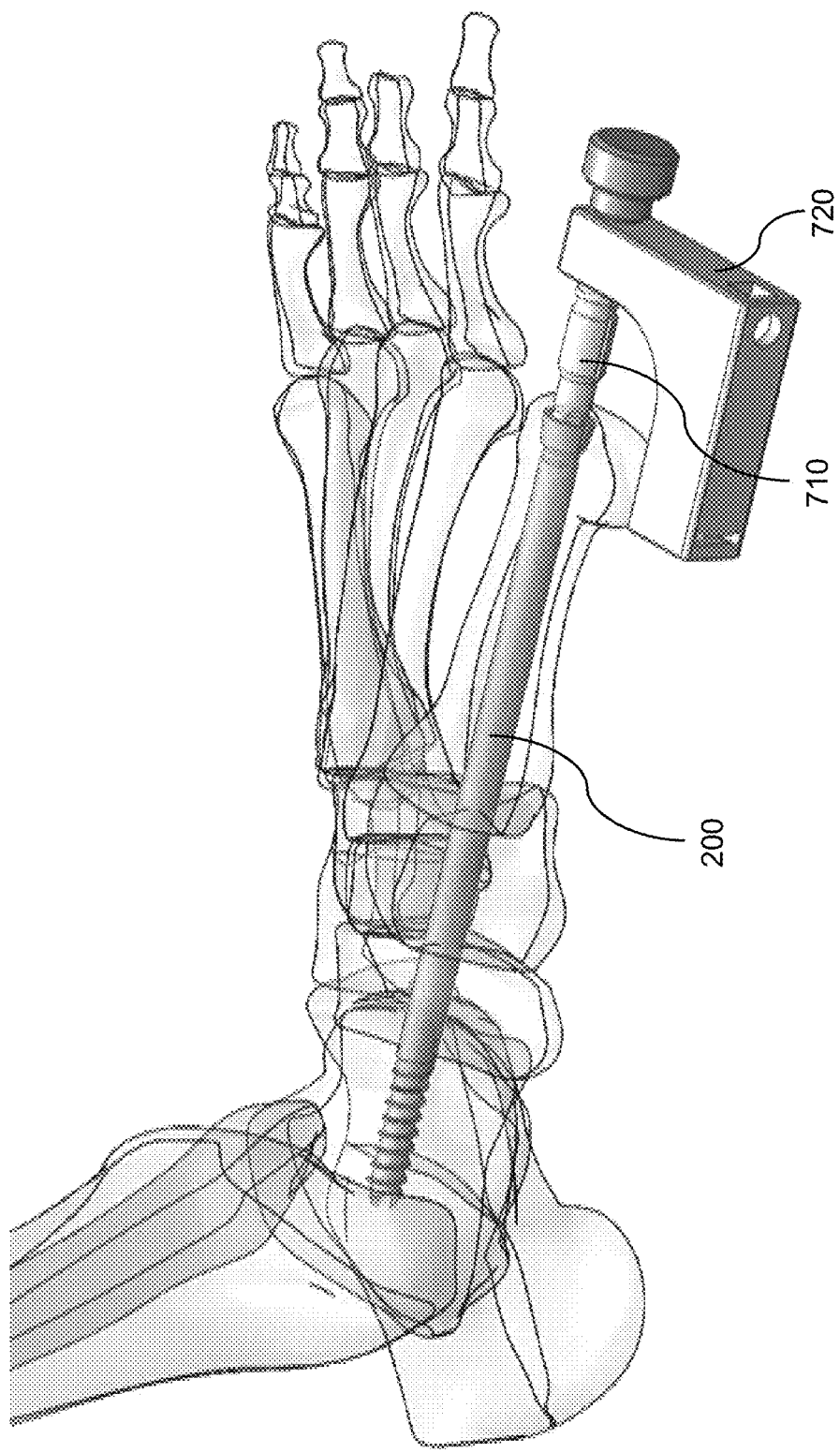
Figure 9:
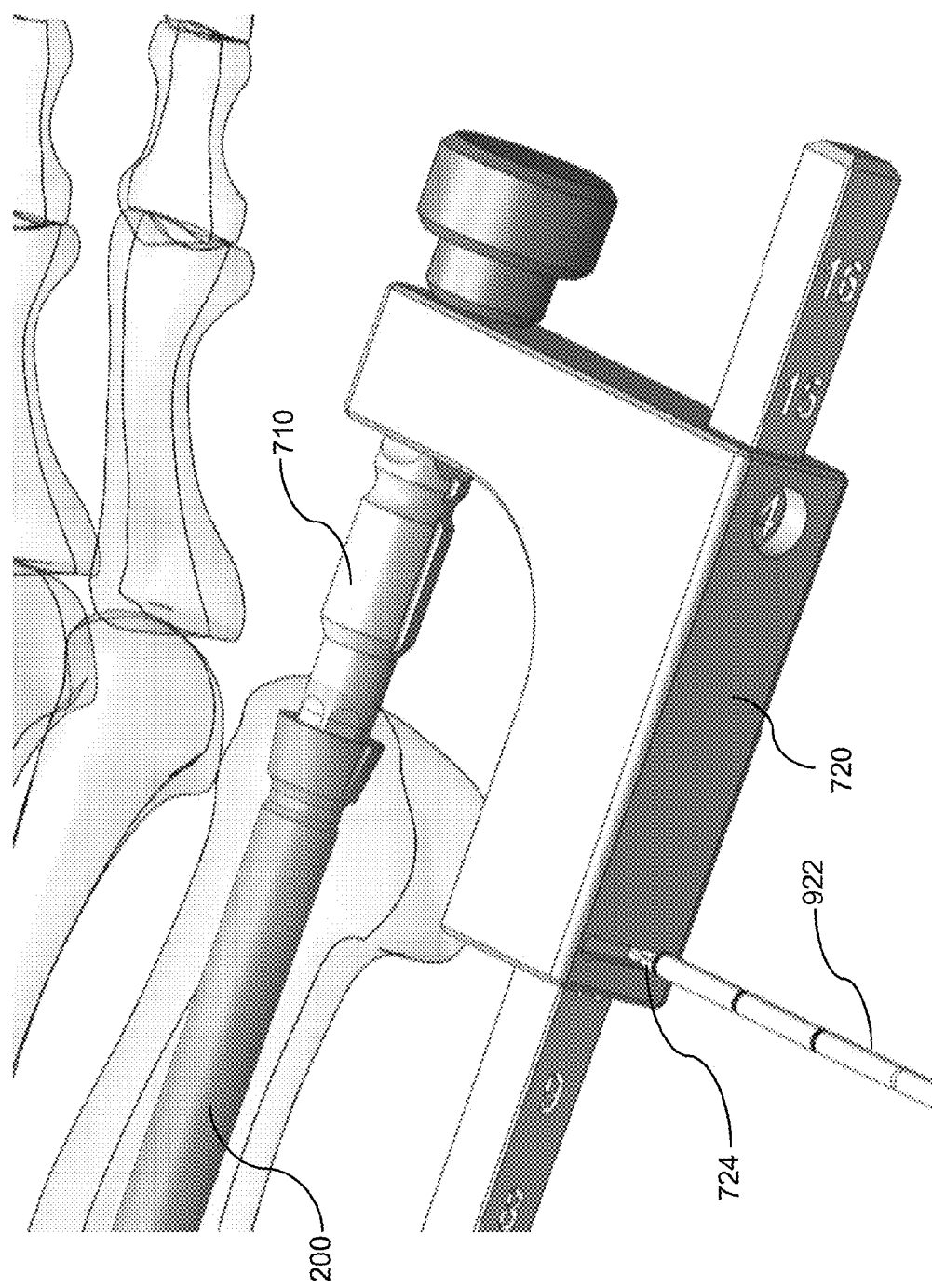
Figure 10:
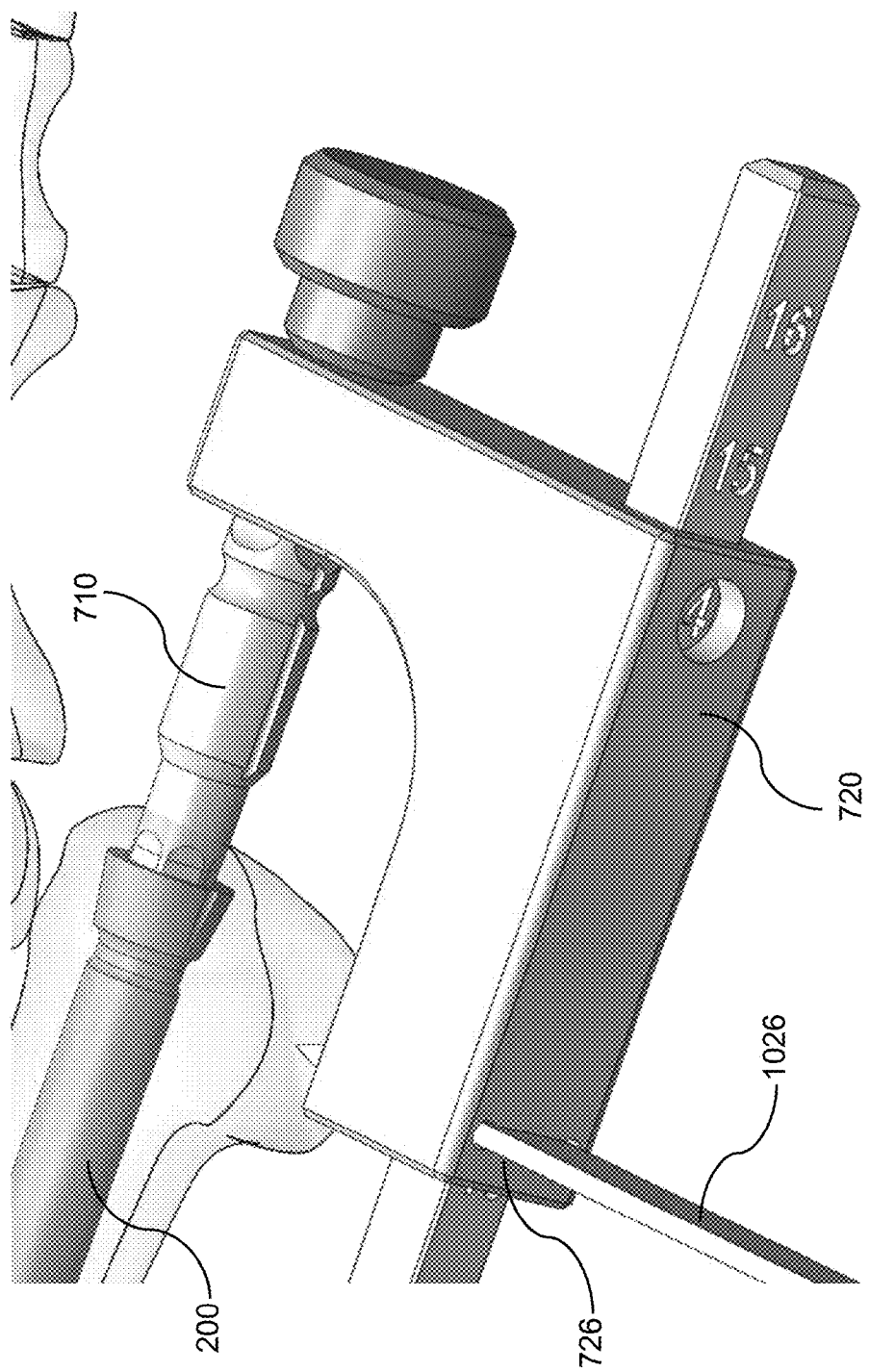
Figure 11:
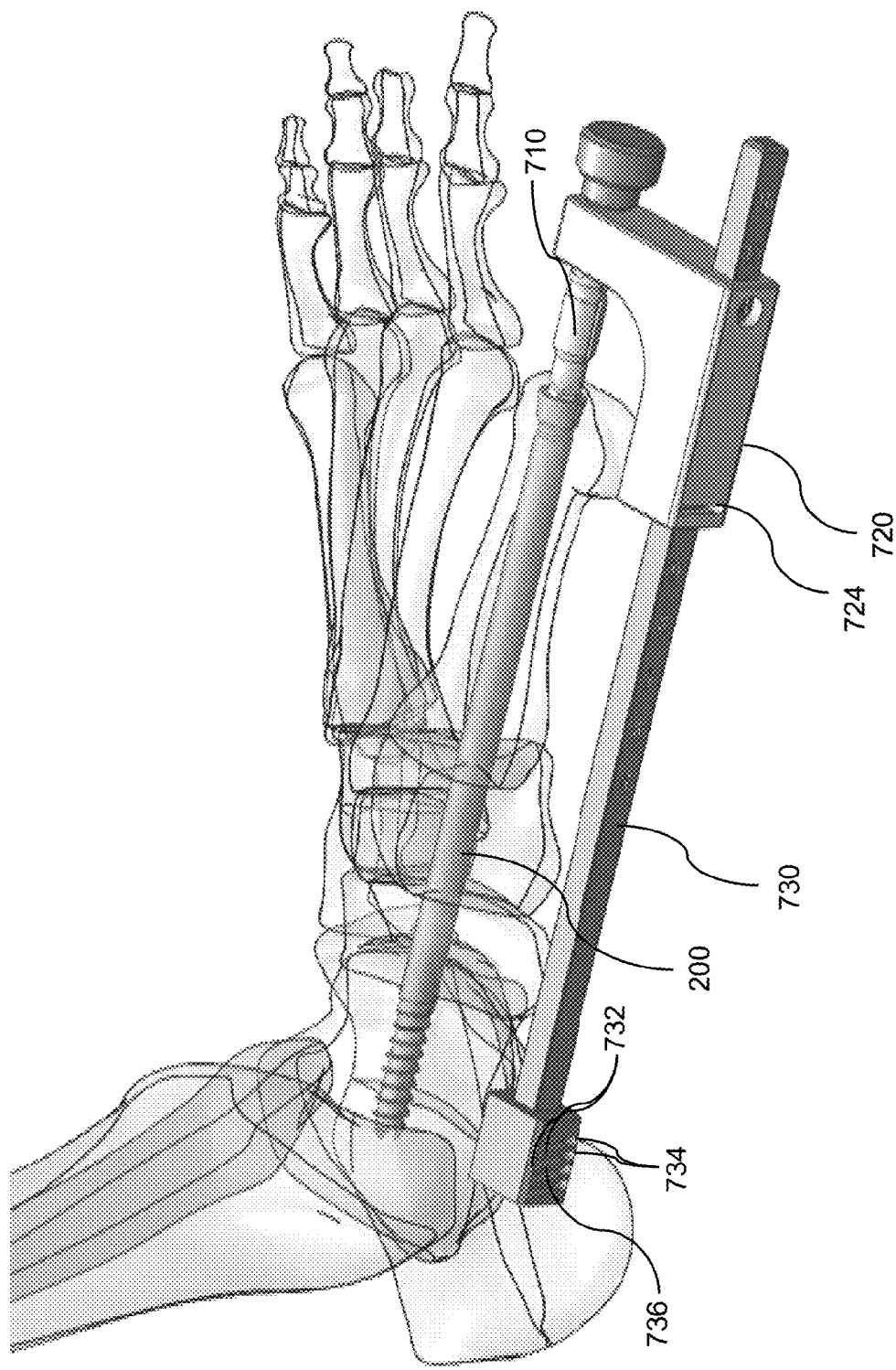

FIG. 8 depicts screw mount 710 and bracket 720 mounted on screw 200. FIG. 9 depicts the use of hole 724 to guide a drill bit 922 in drilling a hole into the cortex adjacent screw 200 in the first position; and FIG. 10 depicts the use of slot 726 to guide an osteotome 1026 in breaking a hole in the cortex around screw 200 at the first position. FIG. 11 depicts screw mount 710, bracket 720 and extension arm 730 cooperating to locate the sets of third and fourth holes 732, 734 and slot 736 at a second position on the screw.

Returning to the flow chart of FIG. 3, at step 380, the two ends of a staple, an open washer, an open nut or the like are inserted into the first and second holes at the first position; and the two ends of one or more staples, open washers, open nuts or the like are inserted into the third and fourth holes at the second position. The staples, washers, nuts as the case may be are then driven at step 385 into their final position in the cortex so that they engage the screw at the first position near the head and engage the screw threads at the second position.

FIG. 12 depicts the profile of an open washer or open nut 1200. FIG. 13 depicts the profile of an open washer or open nut 1300 in position around screw 200. FIG. 14 depicts a staple 1400 in position around screw 200. In each case, each washer or nut 1200, 1300 and each staple 1400 has two spaced-apart ends 1210, 1212; 1310, 1312; 1410, 1412 joined by a middle portion 1214, 1314, 1414, respectively. The middle portion may be straight as in the case of a conventional staple or rounded to varying degrees thereby approximating the curvature of the exterior of the screw. For convenience, the various elements such as staples, open washers, open nuts and the like that may be used in the practice of the invention will be referred to as transverse elements.

Figure 15:
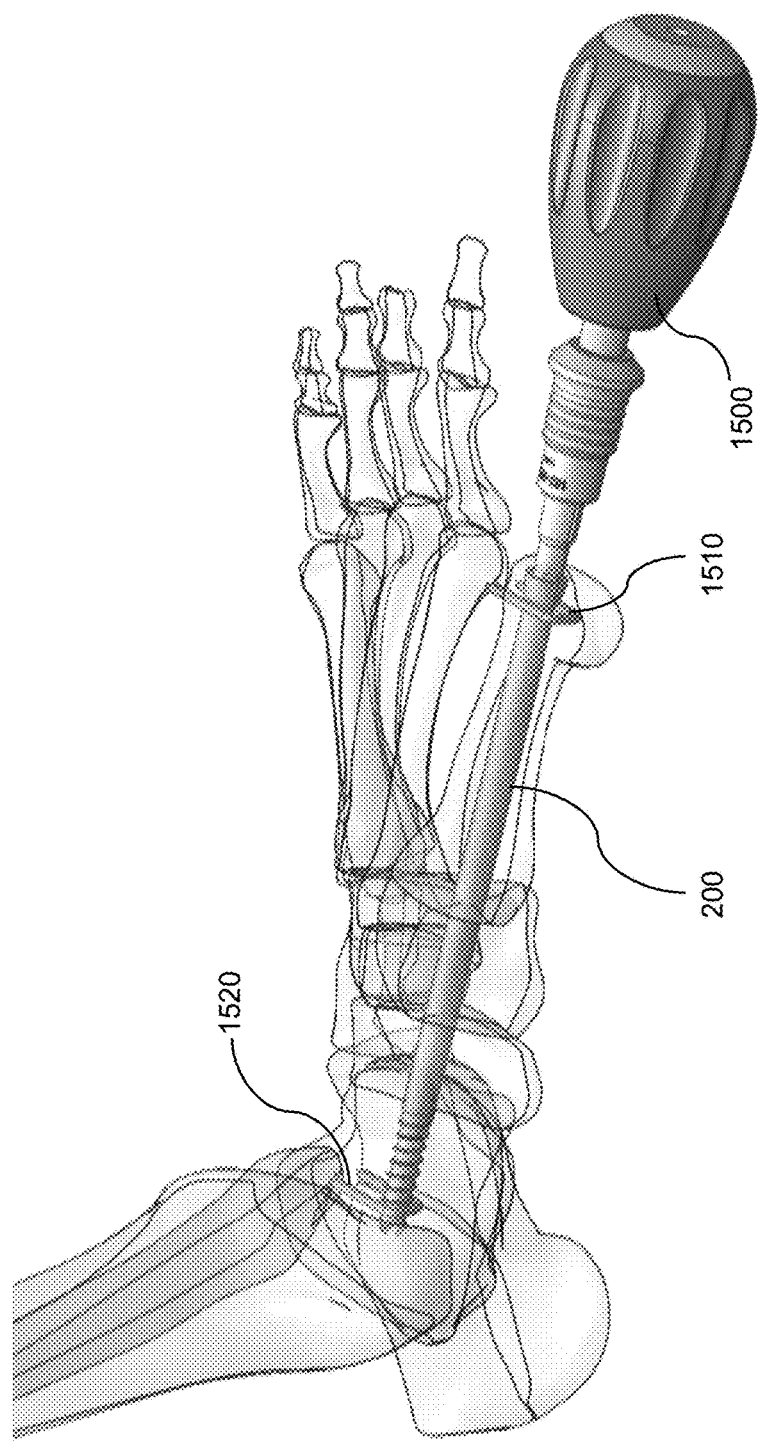

A screw driver is then used at step 390 to turn the screw so as to bring closer together the transverse elements at the first and second position, thereby compressing the bones between these positions. This is illustrated in FIG. 15 which depicts a screw driver 1500 being used to turn screw 200 to move staples 1510 and 1520 closer together. When this step is completed, the screw driver is then removed and the incision is closed at step 395.

As will be apparent to those skilled in the art, numerous variations may be practiced within the spirit and scope of the present invention. For example, a variety of different tools—screw drivers, wrenches, reduction instruments and drill guides—may be used in the practice of the invention. Screws of different sizes and different shapes may be used. Likewise different transverse elements may be used. There may also be variation in the procedure used to implant the screw and transverse elements in the foot. For example, certain steps can be skipped or combined with other steps and certain steps can be performed in a different order. In some procedures it may not be necessary to insert transverse elements at both the first and second positions. For example, it may be possible to develop sufficient compression between the head of the screw and one or more transverse elements located on the screw threads that a transverse element near the head of the screw is not needed. Alternatively, it may be possible to develop sufficient compression between the screw threads and a transverse element mounted near the screw head that one or more transverse elements mounted on the screw threads are not needed. When transverse elements are used at both the first and second positions, the holes can be drilled at the second position before they are drilled at the first position; or it may not be necessary to drill the holes at one or both positions because it may be possible to insert the transverse elements at the appropriate positions around the screw using other devices. Similarly, it may not be necessary to use the osteotome at one or both positions.

The invention claimed is:

1. An assembly for bone fusion, comprising:
a screw member comprising an elongated body extending from a first end to a second end, wherein the elongated body includes first threads near the first end and second threads near the second end;
a first transverse element that engages the first threads of the elongated body of the screw member such that the screw member can be rotated with respect to the first transverse element; and
a second transverse element that engages the second threads of the elongated body of the screw member such that the screw member can be rotated with respect to the second transverse element;
wherein the first transverse element comprises two spaced-apart ends joined by a middle portion.

2. The assembly of claim 1, wherein the first transverse element engages a first bone, wherein the second transverse element engages a second bone, and wherein rotating the screw member brings the first and second transverse elements closer together thereby compressing the first and second bones.

3. The assembly of claim 1, wherein the elongated body is cannulated.

4. The assembly of claim 3, wherein the cannulated elongated body has an interior surface that is threaded.

5. The assembly of claim 1, wherein the elongated body comprises a recess at the first end that is shaped to receive an instrument.

6. The assembly of claim 1, wherein the first and second transverse elements comprise different shapes.

7. An assembly for bone fusion, comprising:
a screw member comprising an elongated body extending from a first end to a second end, wherein the elongated body includes a first continuous thread along the exterior surface of the elongated body near the first end and a second continuous thread along the exterior surface of the elongated body near the second end, wherein the screw member is inserted in a bore extending through at least a first bone and a second bone;
a first transverse element that engages the first continuous thread such that the screw member can be rotated with respect to the first transverse element, wherein the first transverse element engages the first bone; and
a second transverse element that engages the second continuous thread such that the screw member can be rotated with respect to the second transverse element, and wherein rotating the screw member brings the first and second transverse elements closer together thereby compressing the first and second bones;
wherein the first transverse element comprises two spaced-apart ends joined by a middle portion.

8. The assembly of claim 7, wherein the elongated body is cannulated.

9. The assembly of claim 8, wherein the cannulated elongated body has an interior surface that is threaded.

10. The assembly of claim 7, wherein the elongated body comprises a recess at the first end that is shaped to receive an instrument.

11. The assembly of claim 7, wherein the first and second transverse elements comprise different shapes.

12. An assembly for bone fusion, comprising:
a screw member comprising an elongated body extending from a first end to a second end, having threads at the first end and threads at to the second end;
a first transverse element that engages the threads at the first end of the elongated body of the screw member such that the screw member can be rotated with respect to the first transverse element; and
a second transverse element that engages the threads at the second end of the elongated body of the screw member such that the screw member can be rotated with respect to the second transverse element;
wherein rotating the screw member brings the first and second transverse elements closer together;
wherein the first transverse element comprises two spaced-apart ends joined by a middle portion.

13. The assembly of claim 12, wherein the elongated body is cannulated.

14. The assembly of claim 13, wherein the cannulated elongated body has an interior surface that is threaded.

15. The assembly of claim 12, wherein the elongated body comprises a recess at the first end that is shaped to receive an instrument.

16. The assembly of claim 12, wherein the first and second transverse elements comprise different shapes.

17. The assembly of claim 13 wherein the first and second transverse elements comprise different shapes.

* * * * *